(12) United States Patent
Alva

(10) Patent No.: US 8,469,770 B2
(45) Date of Patent: Jun. 25, 2013

(54) MULTIFUNCTION BRASSIERE CUP

(76) Inventor: Dawn Michele Alva, Marina, CA (US)

(*) Notice: Subject to any disclaimer, the term of this patent is extended or adjusted under 35 U.S.C. 154(b) by 445 days.

(21) Appl. No.: 12/785,426

(22) Filed: May 22, 2010

(65) Prior Publication Data

US 2011/0092134 A1    Apr. 21, 2011

Related U.S. Application Data

(60) Provisional application No. 61/279,452, filed on Oct. 20, 2009.

(51) Int. Cl.
*A41C 3/00* (2006.01)

(52) U.S. Cl.
USPC .................................. 450/36; 450/30; 450/31

(58) Field of Classification Search
USPC .................. 450/36, 37–39, 54–58, 1, 30–33
See application file for complete search history.

(56) References Cited

U.S. PATENT DOCUMENTS

| | | | |
|---|---|---|---|
| 155,720 | A | 10/1874 | Gray et al. |
| 684,078 | A | 10/1901 | Martin et al. |
| 949,414 | A | 2/1910 | Cunningham |
| 1,136,727 | A | 4/1915 | Smith et al. |
| 1,189,589 | A | 7/1916 | Lawrence |
| 1,509,226 | A | 9/1924 | Brown |
| 1,670,610 | A | 5/1928 | Colby |
| 2,298,361 | A | 10/1942 | Freund |
| 2,436,430 | A | 2/1948 | Hart |
| 2,440,466 | A | 4/1948 | Freedman |
| 2,452,345 | A | 10/1948 | Anselmo |
| 2,485,313 | A | 10/1949 | Rabinowitz |
| 2,492,862 | A | 12/1949 | Harvey |
| 2,498,487 | A | 2/1950 | Elias |
| 2,501,860 | A | 3/1950 | Becker |
| 2,585,338 | A | 2/1952 | Meares |
| 2,613,355 | A | 10/1952 | Coleman |
| D170,509 | S | 9/1953 | Peck |
| 2,679,048 | A | 5/1954 | Alberts |
| 2,715,225 | A | 8/1955 | Gould |
| 2,890,702 | A | 6/1959 | Farino |

(Continued)

FOREIGN PATENT DOCUMENTS

AU    2006 200 947    9/2006
AU     2006200947    9/2006

(Continued)

OTHER PUBLICATIONS

Catharine Decker, Hands-free Breast Pumping Tip, babylovesyourmilk.com, last modified Jun. 4, 2010, http://babylovesyourmilk.com/hands-free-breast-pumping.php.

(Continued)

*Primary Examiner* — Gloria Hale
(74) *Attorney, Agent, or Firm* — TraskBritt

(57) ABSTRACT

A brassiere includes a multifunction brassiere cup that includes multiple layers partially overlapping one another. A first layer, second layer, and third layer each have unattached edges. The unattached edges of the first and second layers cross to define a nook, which nook is covered by the overlapping third layer. The multifunction brassiere cup is configured to selectively receive a funnel of a breast pump behind the third layer of the cup and within the nook such that the funnel is supported against a nipple by the unattached edges of the first, second, and third layers.

20 Claims, 12 Drawing Sheets

U.S. PATENT DOCUMENTS

| | | | |
|---|---|---|---|
| 2,925,816 | A | 2/1960 | Rosenthal |
| 2,928,396 | A | 3/1960 | O'Dell |
| 3,002,515 | A | 10/1961 | Glogover |
| 3,145,714 | A | 8/1964 | Brown |
| 3,306,299 | A | 2/1967 | Paramore |
| 3,516,415 | A | 6/1970 | Hadley-Webb |
| 3,746,007 | A * | 7/1973 | Hand et al. .................. 450/31 |
| 3,746,008 | A | 7/1973 | LoCascio et al. |
| 3,763,865 | A * | 10/1973 | DeFru ........................... 450/41 |
| 3,773,052 | A | 11/1973 | Belardinelli |
| 3,780,741 | A | 12/1973 | Cole |
| 3,782,385 | A | 1/1974 | Loyd |
| 3,834,397 | A | 9/1974 | Birch |
| 3,840,012 | A | 10/1974 | Rushton, Jr. |
| 3,890,978 | A * | 6/1975 | Nobbs ........................... 450/61 |
| 4,004,294 | A | 1/1977 | Pinch |
| 4,263,912 | A | 4/1981 | Adams |
| 4,270,538 | A | 6/1981 | Murphy |
| 4,335,728 | A | 6/1982 | Fildan |
| 4,355,641 | A | 10/1982 | Dastoli et al. |
| 4,390,024 | A | 6/1983 | Williams |
| 4,393,875 | A | 7/1983 | O'Boyle et al. |
| 4,411,269 | A | 10/1983 | Weintraub |
| 4,423,734 | A | 1/1984 | Schawel |
| 4,453,549 | A | 6/1984 | DiTullio |
| 4,550,734 | A | 11/1985 | Porco |
| 4,584,992 | A | 4/1986 | Liu |
| 4,633,876 | A | 1/1987 | Scullin |
| 4,640,287 | A | 2/1987 | Anderson et al. |
| 4,673,388 | A | 6/1987 | Schlensog et al. |
| 4,713,842 | A | 12/1987 | Patterson |
| 4,857,051 | A | 8/1989 | Larsson |
| 4,878,879 | A | 11/1989 | Kunstadter |
| 4,892,517 | A | 1/1990 | Yuan et al. |
| 4,911,677 | A * | 3/1990 | White ........................... 450/36 |
| 4,929,229 | A | 5/1990 | Larsson |
| 5,009,638 | A | 4/1991 | Riedweg et al. |
| 5,024,628 | A | 6/1991 | Sanchez |
| 5,032,104 | A | 7/1991 | Rainville |
| 5,038,411 | A | 8/1991 | St. Armand |
| 5,045,019 | A | 9/1991 | Capasso et al. |
| 5,049,126 | A | 9/1991 | Larsson |
| D321,273 | S | 11/1991 | Hull |
| 5,071,403 | A | 12/1991 | Larsson |
| 5,090,059 | A | 2/1992 | Kahl |
| 5,092,812 | A | 3/1992 | Babcock |
| 5,094,647 | A | 3/1992 | Courtney |
| 5,167,566 | A | 12/1992 | Novitsky et al. |
| 5,278,998 | A | 1/1994 | Book |
| 5,295,957 | A | 3/1994 | Aida et al. |
| 5,309,572 | A | 5/1994 | Seamans |
| 5,358,476 | A | 10/1994 | Wilson |
| 5,380,238 | A | 1/1995 | Crew-Gee |
| 5,415,632 | A | 5/1995 | Samson |
| D366,351 | S | 1/1996 | Winchell |
| 5,514,166 | A | 5/1996 | Silver et al. |
| 5,571,084 | A | 11/1996 | Palmer |
| 5,575,768 | A | 11/1996 | Lockridge et al. |
| 5,616,125 | A | 4/1997 | Jelks |
| 5,660,577 | A | 8/1997 | Modena |
| 5,664,257 | A | 9/1997 | Hall |
| 5,697,830 | A | 12/1997 | White |
| 5,720,722 | A | 2/1998 | Lockridge |
| 5,823,851 | A | 10/1998 | Dicker |
| 5,941,847 | A | 8/1999 | Huber et al. |
| 5,954,690 | A | 9/1999 | Larsson |
| 6,004,186 | A | 12/1999 | Penny |
| 6,027,396 | A | 2/2000 | Yonchar |
| 6,083,079 | A | 7/2000 | Pearson |
| 6,213,840 | B1 | 4/2001 | Han |
| 6,227,936 | B1 | 5/2001 | Mendoza |
| 6,247,996 | B1 | 6/2001 | Fields |
| D446,629 | S | 8/2001 | Swanger |
| 6,346,027 | B1 | 2/2002 | Merkovsky |
| 6,379,327 | B2 | 4/2002 | Lundy |
| 6,440,100 | B1 | 8/2002 | Prentiss |
| 6,575,202 | B2 | 6/2003 | Lafond |
| 6,652,484 | B1 | 11/2003 | Hunckler et al. |
| 6,659,841 | B2 | 12/2003 | Raimondo |
| 6,706,012 | B2 | 3/2004 | McKendry et al. |
| 6,764,377 | B2 | 7/2004 | Gillan |
| 6,821,185 | B1 | 11/2004 | Francis |
| 6,855,029 | B2 | 2/2005 | Rothman |
| 6,866,558 | B2 | 3/2005 | Luciano et al. |
| 6,887,217 | B1 | 5/2005 | Logan |
| 6,896,581 | B2 | 5/2005 | Otto |
| 6,974,361 | B2 | 12/2005 | Cravaack et al. |
| 7,076,809 | B2 | 7/2006 | Rothman |
| 7,094,217 | B2 | 8/2006 | Fialkoff |
| 7,128,877 | B2 | 10/2006 | Quay et al. |
| 7,223,255 | B2 | 5/2007 | Myers et al. |
| 7,435,155 | B2 * | 10/2008 | Reinisch et al. ................ 450/59 |
| 7,448,936 | B1 | 11/2008 | Kemp-Dorsey |
| 7,559,915 | B2 | 7/2009 | Dao et al. |
| 7,695,343 | B2 * | 4/2010 | Nobbs ........................... 450/33 |
| 8,137,153 | B2 | 3/2012 | Bell |
| 8,192,247 | B2 | 6/2012 | Abbaszadeh |
| 8,323,070 | B2 | 12/2012 | Abbaszadeh |
| 2002/0193731 | A1 | 12/2002 | Myers et al. |
| 2003/0167037 | A1 | 9/2003 | Fialkoff |
| 2003/0191427 | A1 | 10/2003 | Jay et al. |
| 2005/0159701 | A1 | 7/2005 | Conaway |
| 2006/0111664 | A1 | 5/2006 | Samson et al. |
| 2007/0161330 | A1 | 7/2007 | Whitehead et al. |
| 2008/0039781 | A1 | 2/2008 | Bjorge |
| 2010/0159802 | A1 | 6/2010 | Abbaszadeh |
| 2011/0314587 | A1 | 12/2011 | Ritchie |

FOREIGN PATENT DOCUMENTS

| | | |
|---|---|---|
| DE | 584456 | 9/1933 |
| EP | 0 752 213 | 1/1997 |
| EP | 0 941 674 | 9/1999 |
| FR | 1.004.058 | 3/1952 |
| GB | 2 287 640 | 9/1995 |
| WO | 9953780 | 10/1999 |
| WO | WO 2010/070042 | 6/2010 |

OTHER PUBLICATIONS

International Search Report for PCT/US2010/053075, Jan. 24, 2011, European Patent Office.

Written Opinion of the International Searching Authority for PCT/US2010/053075, Jan. 24, 2011, European Patent Office.

International Search Report PCT/US2010/053075 dated Jan. 24, 2010.

Written Opinion PCT/US2010/053075 dated Jan. 24, 2010.

* cited by examiner

MULTIFUNCTION BRASSIERE CUP

CROSS-REFERENCE TO RELATED APPLICATION

This application claims priority to U.S. Provisional Application Ser. No. 61/279,452, filed Oct. 20, 2009, titled "Multiple Function Nursing Bra Cup," the disclosure of which is incorporated herein by reference.

FIELD

The present disclosure generally relates to apparel worn by a nursing woman, and, more particularly, to a brassiere cup configured to accommodate a nursing woman's use of a breast pump.

BACKGROUND

Because of the increased awareness of the health benefits of breastfeeding for both infant and mother, many women are finding ways to provide their infants with breast milk even if the mothers are not physically present during the delivery of the milk to the infants or not physically able to directly breastfeed their infants. To do this, typically, a woman will express milk using a manual or electric breast pump device that has a funnel. The funnel is placed over the nipple of the breast, and suction is applied by the breast pump to encourage expression of milk from the nipple. A traditional electronic breast pump includes the funnel, a motor to generate the suction for the expression of milk, and a reservoir connected to the funnel to receive the expressed milk. Because of the duration and frequency required for breast milk expression, a woman may express both breasts simultaneously to increase efficiency. This process is often uncomfortable and time consuming. Further, without additional support, the funnel of a traditional breast pump often will not remain over the nipple on the breast; therefore, use of the pump usually does not allow the nursing woman to perform other activities simultaneously.

BRIEF SUMMARY

The multifunction brassiere cup of the present disclosure provides a cup configured to receive and support a funnel of a conventional breast pump against a nipple of a breast to allow for hands-free pumping. The cup of the brassiere includes multiple layers arranged to partially overlap one another, each layer having an unattached edge. When the funnel is selectively received by the cup, the unattached edges of the layers each provide support for the funnel. Therefore, the funnel is supported, from multiple angles and sides, to remain positioned over the nipple while also being supported against the nipple by the multiple layers.

According to the embodiments described below, the multifunction brassiere cup includes a bottom layer that is partially overlapped by a middle layer that is partially overlapped by a top layer. The unattached edges of the bottom layer and the middle layer are arranged so as to cross over one another, thereby defining a nook. The top layer is arranged so as to cover the nook. The cup is further configured to receive the funnel of a breast pump underneath the unattached edge of the top layer and within the nook behind the unattached edges of the middle and bottom layers. Accordingly, the funnel of the breast pump may be selectively received by the multifunction brassiere cup while the brassiere incorporating the cup is being worn by the nursing woman. Likewise, the funnel may be selectively removed from the multifunction brassiere cup while the brassiere is still being worn.

The material of the layers may be stretchable. In some embodiments, two of the layers are stretchable. In other embodiments, all of the layers are stretchable. In still other embodiments, only the unattached edges of two of the layers are stretchable, and in other embodiments, only the unattached edges of each of the layers are stretchable. As such, the stretch of the unattached edges of the respective layers for receipt of the funnel results in an elastic-like pull against the funnel, itself, when it is in place over the nipple, from the at least two unattached edges. According to the illustrated embodiments, the unattached edge of the top layer discourages the funnel from slipping farther away from the cup's lower edge, the unattached edge of the middle layer discourages the funnel from slipping farther away from the cup's upper central edge, and the unattached edge of the bottom layer discourages the funnel from slipping farther away from the cup's upper outer edge. The elasticity of the stretchable material of each of the layers or unattached edges, whether in embodiments in which the material or unattached edges of each of the layers are stretchable or in embodiments in which the material or unattached edges of just some of the layers are stretchable, further discourages the funnel from slipping outwardly away from the nipple or breast. The cup is further configured, in this way, to accommodate the natural expansion and contraction of a nursing woman's breasts as well as the natural variations in nipple locations on various women's breasts.

In some embodiments, the cup is included in a brassiere utilizing two such cups and traditional shoulder straps. In other embodiments, the multifunction brassiere cup is included in brassieres of other configurations, such as halter tops, tank-tops, brassiere-top swimming suits, sports brassieres, and the like. In some embodiments, only one multifunction brassiere cup is included in the brassiere.

In some embodiments, the brassiere in which the multifunction brassiere cup is included further includes at least one selectively releasable clasp that selectively connects the shoulder, neck, or other upper-support strap of the brassiere to a side support strap. Unclasping a selectively releasable clasp disconnects the layers of the cup from the shoulder strap, allowing all of the layers of the cup to be lowered so as to uncover the breast and nipple while the side support strap continues to secure the shoulder strap in its place and, in some embodiments, to support the breast. In this way, a wearer can directly nurse an infant with manipulation of only one clasp, while the layers of the cup remain connected to one another, without having to remove the brassiere, without having to detach the multifunction brassiere cup from the brassiere, and without having to detach any part of the brassiere from the rest of the brassiere.

Also, the top layer of the multifunction brassiere cup may be configured to cover and conceal the nipple and the majority of the breast when the top layer is not being stretched. As such, the brassiere containing the multifunction brassiere cups may have a visible appearance akin to the appearance of a traditional brassiere. Further, the bottom layer of the multifunction brassiere cup may be configured to cover the nipple and the majority of the breast when the bottom layer is not being stretched. Accordingly, when the top layer of the cup is stretched so as to insert the funnel of a breast pump, the nipple may not be exposed, but may remain covered and concealed by the bottom layer of the cup.

Thus, the multifunction brassiere cup of embodiments of the present disclosure provides a supportive garment that may be worn in the same manner as a traditional brassiere, e.g., for long periods of time as an undergarment to outerwear. It may allow for quick and easy, hands-free use of a breast pump or a pair of breast pumps without having to disrobe or otherwise remove the brassiere or any other part of the brassiere. The central area of the multifunction brassiere cup may comprise only material, thereby adding to the relative comfort of the multifunction brassiere cup. Further, the configuration of the cup may allow a wearer to support the funnel against her nipple, hands free, regardless of whether the nipple is located in the exact center of the breast or is offset somewhat. Still further, because the funnel is supported by each of the layers of the cup itself, the wearer may not need to hassle with separate attachment mechanisms or attachment devices such as hooks, buttons, zippers, hook and loop connections, or the like. Also, the multiple layers of the cup support the funnel from multiple directions, which may decrease the likelihood that the funnel will move away from the nipple undesirably.

The purpose of the Brief Summary is to enable the public and particularly scientists, engineers, and practitioners in the art who are not familiar with patent or legal terms or phraseology to determine quickly, from a cursory inspection, the nature and essence of the technical disclosure of the application. The Brief Summary is neither intended to define the multifunction brassiere cup, nor is it intended to be limiting as to the scope of the present disclosure in any way.

Still other features and advantages of the claimed multifunction brassiere cup will become readily apparent to those skilled in the art from the following detailed description describing embodiments of the multifunction brassiere cup, simply by way of illustration of the best mode contemplated by carrying out the multifunction brassiere cup. As will be realized, the multifunction brassiere cup is capable of modification in various obvious respects all without departing from the present disclosure. Accordingly, the drawings and description of the embodiments are to be regarded as illustrative and not restrictive.

DETAILED DESCRIPTION

Figure 1:
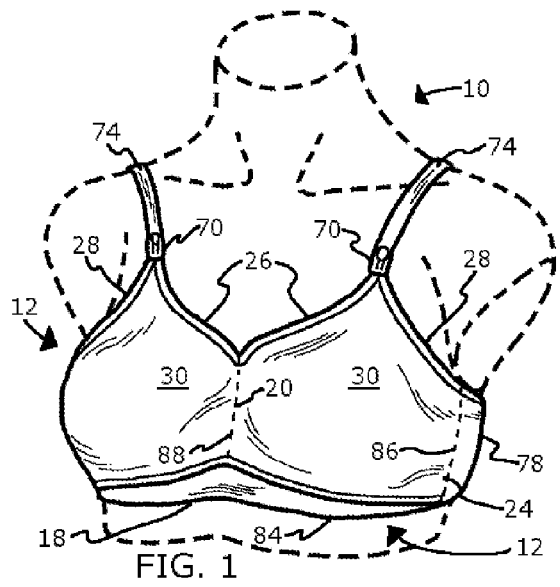
FIG. 1 is a perspective, front elevational view of a brassiere with multifunction brassiere cups according to a first embodiment.

While the multifunction brassiere cup is susceptible of various modifications and alternative constructions, certain embodiments thereof have been illustrated in the drawings and will be described below in detail. It should be understood, however, that there is no intention to limit the present disclosure to the specific forms disclosed and illustrated, but, to the contrary, the present disclosure is to cover all modifications, alternative constructions, and equivalents falling within the spirit and scope of the present disclosure, including the claims below.

As shown in the figures, for purpose of illustration, the multifunction brassiere cup may be embodied in overlapping layers having unattached edges so as to define a nook configured to receive a funnel of a breast pump and to support the funnel against a nipple of a breast during the expression of milk. When received in the multifunction brassiere cup, the funnel may be supported in position over the nipple and against the breast by each of the three layers. The elasticity of the layers or the unattached edges thereof may allow for flexibility in the positioning of the funnel while still providing sufficient support for the funnel to allow for hands-free use of the breast pump.

In the following description and in the figures, like elements are identified with like reference numerals. The use of "e.g.," "etc.," and "or" indicates non-exclusive alternatives without limitation unless otherwise noted. The use of "including" means "including, but not limited to," unless otherwise noted.

Embodiments of the multifunction brassiere cup are illustrated in FIGS. 1 through 34, both as a stand-alone cup and as incorporated within a brassiere. A first embodiment of the multifunction brassiere cup is illustrated in FIGS. 1 through 5, 7 through 26, and 28 through 33. As illustrated in FIGS. 1 through 4, the cup 12 includes a cup lower edge 18, which is illustrated as passing essentially under the breast; a cup side central edge 20, which is illustrated as being the side of the cup 12 that is proximate to the sternum of the wearer of the cup 12; a cup side outer edge 24, which is illustrated as being the side of the cup 12 that is proximate to the arm of the wearer of the cup 12; a cup upper central edge 26, which is illustrated as the upper side that is proximate to the sternum of the wearer; and a cup upper outer edge 28, which is illustrated as the upper side that is proximate to the arm of the wearer. As shown, therefore, the cup side central edge 20 extends from the cup lower edge 18 to the cup upper central edge 26, the cup upper central edge 26 extends from the cup side central edge 20 to the cup upper outer edge 28, the cup upper outer edge 28 extends from the cup upper central edge 26 to the cup side outer edge 24, and the cup side outer edge 24 extends from the cup upper outer edge 28 to the cup lower edge 18.

Figure 2:
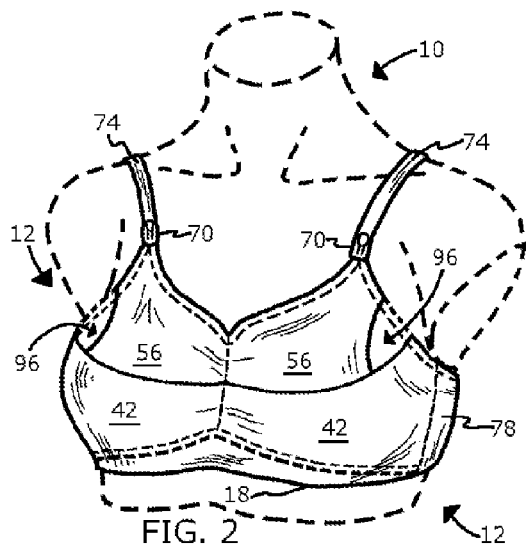
FIG. 2 is a perspective, front elevational view of the brassiere with multifunction brassiere cups according to the first embodiment with a top layer shown in broken line.
Figure 3:
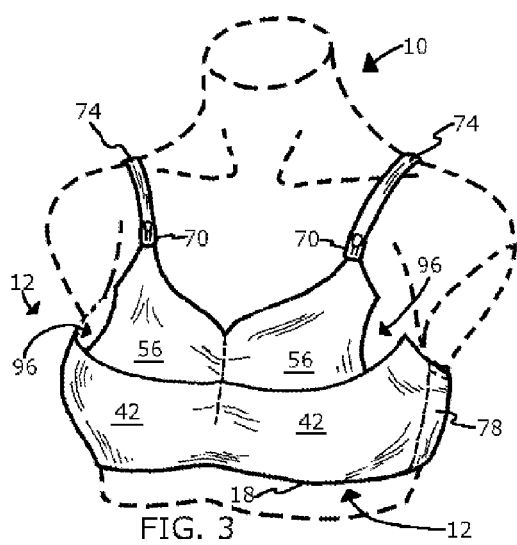
FIG. 3 is a perspective, front elevational view of the brassiere with multifunction brassiere cups according to the first embodiment with the top layer removed.

As shown in FIGS. 1 through 4, the cup 12 is formed by overlapping layers. That is, a first layer, such as the illustrated bottom layer 56 (FIG. 4), is partially overlapped by a second layer, such as the illustrated middle layer 42, as shown in FIG. 3. A third layer, such as the illustrated top layer 30 (FIG. 1), partially overlaps the second and first layers, i.e., the middle layer 42 and the bottom layer 56, as shown in FIG 2. As arranged, the bottom layer 56 of the cup 12 may not be visible from a front view of the cup 12 when a funnel 7 (see FIG. 27) is not received within the cup 12, as shown in FIG. 1.

Figure 7:
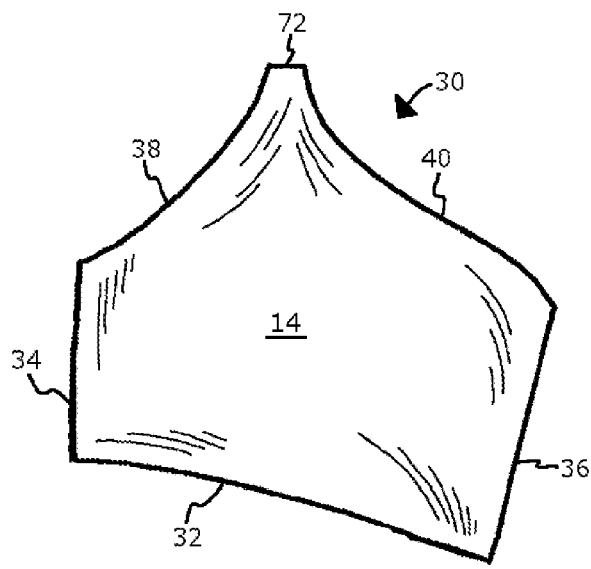
FIG. 7 is a back elevational view of the top layer of a left-side multifunction brassiere cup according to the first embodiment and is a mirror view of the back elevational view of the top layer of a right-side multifunction brassiere cup according to the first embodiment.

More particular back views of the layers of the cup 12 are shown in FIGS. 7 through 17. FIG. 7 shows a back view of a top layer 30 of a left-side cup 12, such as the cup 12 shown to the left-hand side of FIG. 1. The top layer 30 includes a top layer lower edge 32, a top layer side central edge 34 extending from the top layer lower edge 32, and a top layer upper central edge 38 extending from the top layer side central edge 34. The top layer 30 also includes a top layer side outer edge 36 extending from the top layer lower edge 32 and includes a top layer upper outer edge 40 extending from the top layer side outer edge 36. A clasp attachment point 72 is located adjacent the top layer upper central edge 38 and the top layer upper outer edge 40. When constructed in the cup 12, the top layer side central edge 34 aligns along the cup side central edge 20, the top layer upper central edge 38 aligns along the cup upper central edge 26, the top layer upper outer edge 40 aligns along the cup upper outer edge 28, and the top layer side outer edge 36 aligns along the cup side outer edge 24. The top layer 30 may be made of a first material 14 that may be decorative, so as to add to the aesthetics of the cup 12 when included in a brassiere 10 (see FIG. 1).

Figure 8:
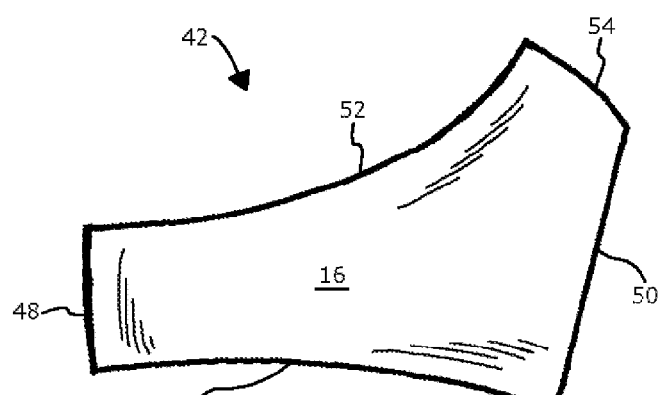
FIG. 8 is a back elevational view of the middle layer of the left-side multifunction brassiere cup according to the first embodiment and is a mirror view of the back elevational view of the middle layer of the right-side multifunction brassiere cup according to the first embodiment.

FIG. 8 shows a back view of the middle layer 42 of the left-side cup 12, such as the cup 12 shown to the left-hand side of FIG. 1. The middle layer 42 includes a middle layer lower edge 46, a middle layer side central edge 48 extending from the middle layer lower edge 46, and a middle layer upper central edge 52 extending from the middle layer side central edge 48. The middle layer 42 further includes a middle layer side outer edge 50 extending from the middle layer lower edge 46 and includes a middle layer upper outer edge 54 extending from the middle layer side outer edge 50. According to the first illustrated embodiment, the middle layer upper central edge 52 and the middle layer upper outer edge 54 also directly extend from one another. When constructed in the cup 12, the middle layer lower edge 46 aligns along the cup lower edge 18, the middle layer side central edge 48 aligns along part of the cup side central edge 20, the middle layer side outer edge 50 aligns along the cup side outer edge 24, and the middle layer upper outer edge 54 aligns along part of the cup upper outer edge 28. According to the illustrated embodiment, in construction, the middle layer side central edge 48 extends from the cup lower edge 18 to a central side midpoint 22 (FIG. 12) on the cup side central edge 20. The middle layer 42 may be constructed of an exterior layer of the first material 14 and an interior layer of a second material 16. Ideally, the exterior layer of the middle layer 42 is made of the same material used to construct the top layer 30 so that, when viewed in the constructed brassiere 10, the exteriorly-visible material matches.

Figure 9:
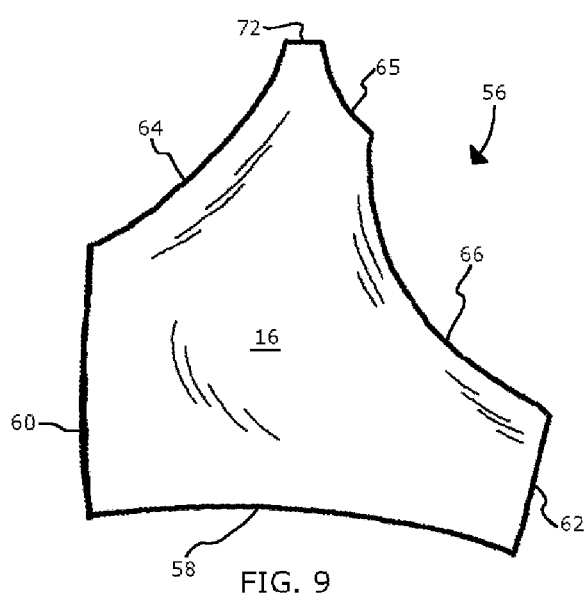
FIG. 9 is a back elevational view of a bottom layer of the left-side multifunction brassiere cup according to the first embodiment and is a mirror view of the back elevational view of a bottom layer of the right-side multifunction brassiere cup according to the first embodiment.

FIG. 9 illustrates a back view of the bottom layer 56 of the left-side cup 12, such as the cup 12 shown to the left-hand side of FIG. 1. The bottom layer 56 includes a bottom layer lower edge 58, a bottom layer side central edge 60 extending from the bottom layer lower edge 58, and a bottom layer upper central edge 64 extending from the bottom layer side central edge 60. The bottom layer 56 further includes a bottom layer side outer edge 62 extending from the bottom layer lower edge 58, a bottom layer upper outer edge 66 extending from the bottom layer side outer edge 62, and a bottom layer upper clasp edge 65 extending from the bottom layer upper outer edge 66. Another clasp attachment point 72 is located adjacent to the bottom layer upper central edge 64 and bottom layer upper clasp edge 65. When constructed, the bottom layer lower edge 58 aligns along the cup lower edge 18, the bottom layer side central edge 60 aligns along the cup side central edge 20, the bottom layer upper central edge 64 aligns along the cup upper central edge 26, the bottom layer side outer edge 62 aligns along part of the cup side outer edge 24, and the bottom layer upper clasp edge 65 aligns along part of the cup upper outer edge 28. According to the illustrated embodiment, in construction, the bottom layer side outer edge 62 extends from the cup lower edge 18 to an outer side midpoint 23 (FIG. 14) on the cup side central edge 20. Further, according to the illustrated embodiment, in construction, the bottom layer upper clasp edge 65 extends from the clasp attachment point 72 approximately a third of the length of the cup upper outer edge 28. Because the bottom layer 56 may not be visible from the front of the constructed cup 12, according to the illustrated embodiment of FIG. 1, the bottom layer 56 may be constructed from the second material 16.

Figure 10:
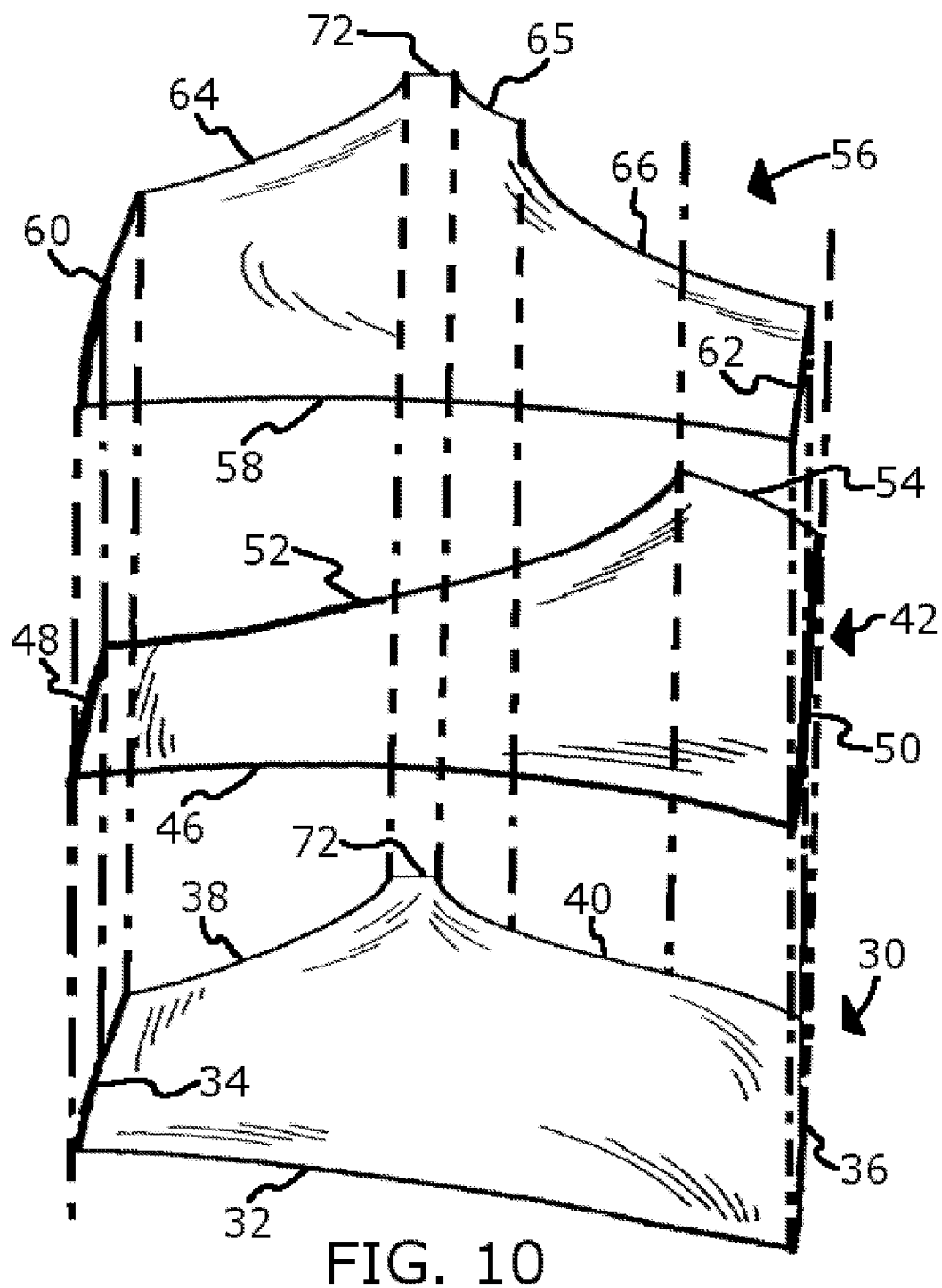
FIG. 10 is an exploded, perspective view of the back sides of the layers of the left-side multifunction brassiere cup according to the first embodiment and is a mirror view of an exploded, perspective view of the back sides of the layers of the right-side multifunction brassiere cup according to the first embodiment.

FIG. 10 shows an exploded view of the three layers of the left-side cup 12 as they are arranged to partially overlap one another. FIGS. 11 through 14 further show the arrangement of the three layers in the constructed cup 12. As shown, the middle layer 42 partially overlaps the bottom layer 56 and is arranged so that the middle layer upper central edge 52 and bottom layer upper outer edge 66 cross one another, thereby defining a nook 96 (see FIGS. 2, 3, and 14 through 17). The top layer 30 partially overlaps the middle layer 42 and the bottom layer 56 and covers the nook 96.

Figure 15:
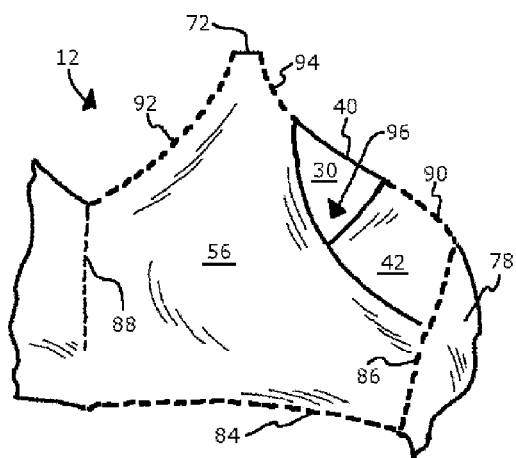
FIG. 15 is partial, back elevational view of the left-side multifunction brassiere cup incorporated within the brassiere according to the first embodiment and is a mirror view of the partial, back elevational view of the right-side multifunction brassiere cup incorporated within the brassiere according to the first embodiment.

FIG. 15 shows a partial view of the constructed cup 12 incorporated within the brassiere 10. Again, the cup 12 illustrated is the left-side cup 12, such as the cup 12 shown to the left-hand side of FIG. 1. In construction, a first seam 84 connects the bottom layer 56 to the middle layer 42 along the cup lower edge 18, joining the bottom layer lower edge 58 to the middle layer lower edge 46. A second seam 86 connects the bottom layer 56, middle layer 42, and top layer 30 to one another along the cup side outer edge 24, joining the bottom layer side outer edge 62 to part of the middle layer side outer edge 50 and part of the top layer side outer edge 36 while joining the middle layer side outer edge 50 to the top layer side outer edge 36. According to the illustrated embodiment, the bottom layer side outer edge 62 is connected along the cup side outer edge 24 from the cup lower edge 18 to an outer side midpoint 23.

A third seam 88 connects the bottom layer 56, the middle layer 42, and the top layer 30 along the cup side central edge 20, joining the bottom layer side central edge 60 to the middle layer side central edge 48 and to the top layer side central edge 34. Because, according to the illustrated embodiment, the middle layer side central edge 48 extends from the cup lower edge 18 to the central side midpoint 22, the middle layer side central edge 48 joins a part of the bottom layer side central edge 60 and a part of the top layer side central edge 34. Further, according to the illustrated embodiment, the length of the top layer side central edge 34 is less than that of the bottom layer side central edge 60; thus, the top layer side central edge 34 joins a part of the bottom layer side central edge 60.

Also as shown in FIG. 15, a fourth seam 90 connects the middle layer 42 to the top layer 30 along part of the cup upper outer edge 28, joining the middle layer upper outer edge 54 to part of the top layer upper outer edge 40. According to the illustrated embodiment, the middle layer upper outer edge 54 is joined along approximately a third of the top layer upper outer edge 40. A fifth seam 92 connects the bottom layer 56 to the top layer 30 along the cup upper central edge 26, joining the bottom layer upper central edge 64 to the top layer upper central edge 38. A sixth seam 94 connects the bottom layer 56 to the top layer 30 along part of the cup upper outer edge 28, joining the bottom layer upper clasp edge 65 to part of the top layer upper outer edge 40. According to the illustrated embodiment, the bottom layer upper clasp edge 65 is joined along approximately a third of the top layer upper outer edge 40. Therefore, the portion of the top layer upper outer edge 40 extending between the bottom layer upper clasp edge 65 and middle layer upper outer edge 54 is left unconnected to another layer of the cup 12. Further, in construction, the top layer lower edge 32, middle layer upper central edge 52, and bottom layer upper outer edge 66 are left unattached to another layer of the cup 12.

Figure 5:
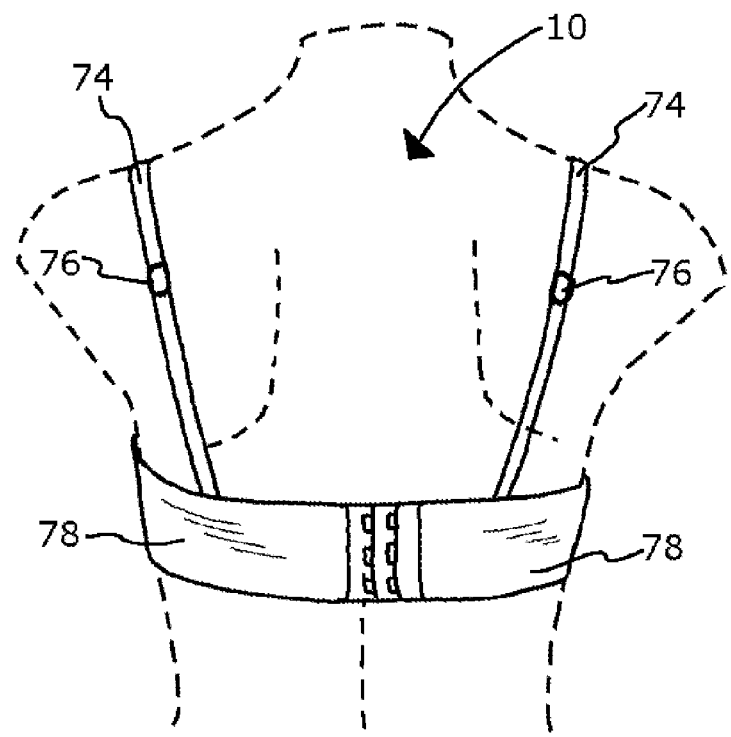
FIG. 5 is a back elevational view of the brassiere with multifunction brassiere cups according to the first embodiment.
Figure 6:
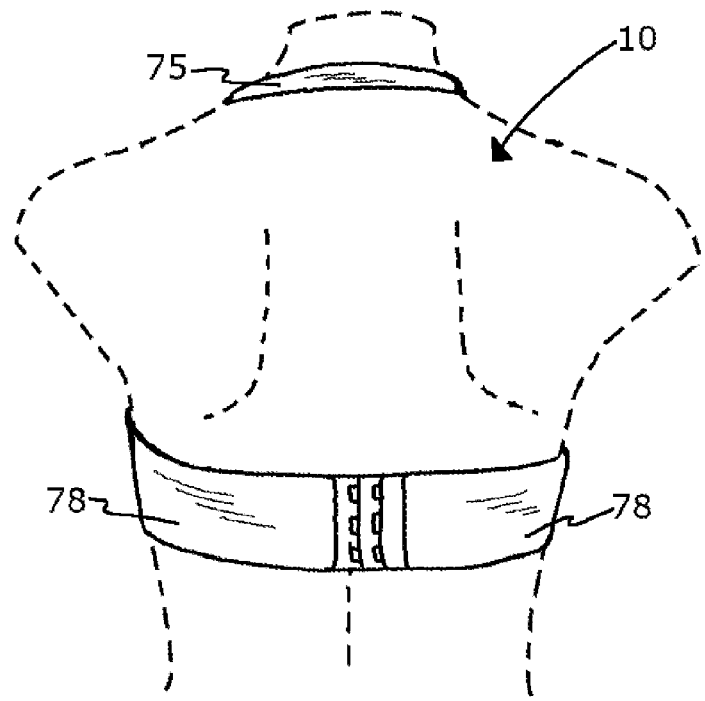
FIG. 6 is a back elevational view of a brassiere with multifunction brassiere cups according to a second embodiment.
Figure 16:
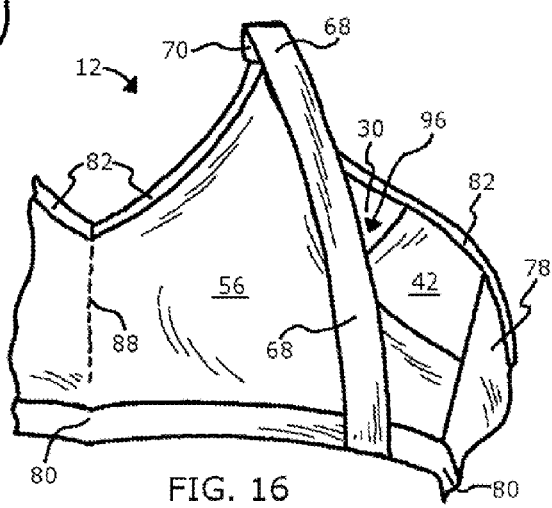
FIG. 16 is a partial, back elevational view of the left-side multifunction brassiere cup incorporated within the brassiere according to the first embodiment and is a mirror view of the partial, back elevational view of the right-side multifunction brassiere cup incorporated within the brassiere according to the first embodiment, with edging, a side support strap, and a frame support incorporated therewith.

As shown in FIG. 16, the cup 12 may be configured to be incorporated within a brassiere (e.g., brassiere 10). According to the first illustrated embodiment, as shown in FIG. 5, the brassiere 10 may be a conventional brassiere 10 having an adjustable back band 78, a pair of shoulder straps 74, and a pair of strap length adjusters 76, each configured to allow for length adjustments to the shoulder straps 74. According to the second illustrated embodiment, as shown in FIG. 6, the brassiere 10 may be a halter-style brassiere, having the adjustable back band 78 and a neck strap 75. In other embodiments, the cup 12 may be incorporated in a strapless brassiere, a cross-strapped brassiere, a sports brassiere, or a brassiere portion of a bathing suit, leotard, tank-top, or the like.

Figure 11:
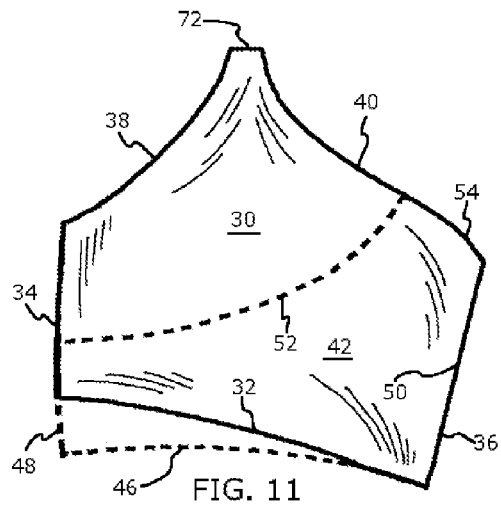
FIG. 11 is a back elevational view of the middle layer, shown in dashed line, overlapping the top-layer of the left-side multifunction brassiere cup according to the first embodiment and is a mirror view of the back elevational view of the middle layer, shown in dashed line, overlapping the top layer of the right-side multifunction brassiere cup according to the first embodiment.
Figure 12:
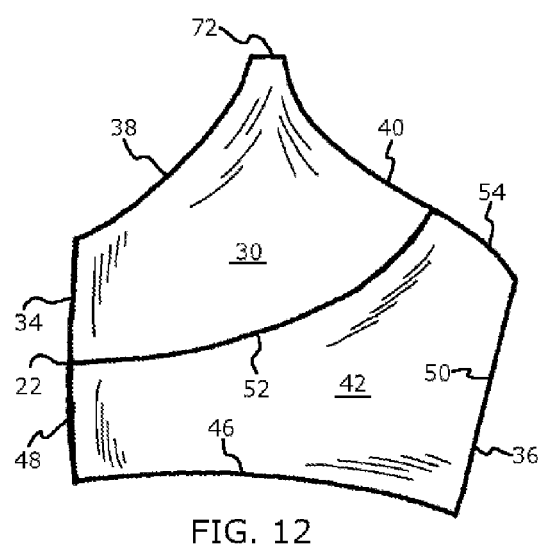
FIG. 12 is a back elevational view of the middle layer overlapping the top layer of the left-side multifunction brassiere cup according to the first embodiment and is a mirror view of the back elevational view of the middle layer overlapping the top layer of the right-side multifunction brassiere cup according to the first embodiment.
Figure 13:
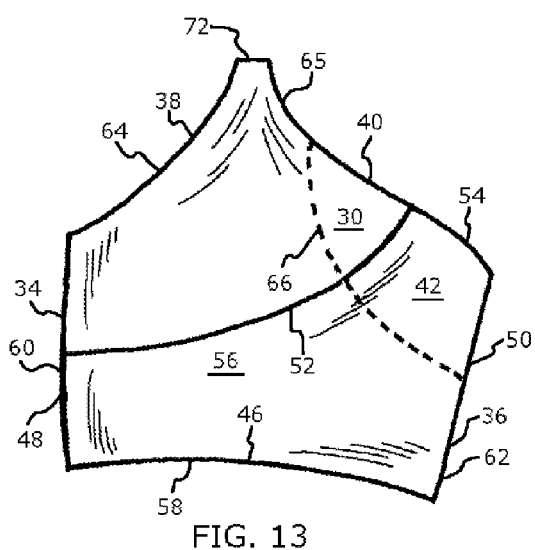
FIG. 13 is a back elevational view of the bottom layer, shown in dashed line, overlapping the middle layer and the top layer of the left-side multifunction brassiere cup according to the first embodiment and is a mirror view of the back elevational view of the bottom layer, shown in dashed line, overlapping the middle layer and the top layer of the right-side multifunction brassiere cup according to the first embodiment.
Figure 14:
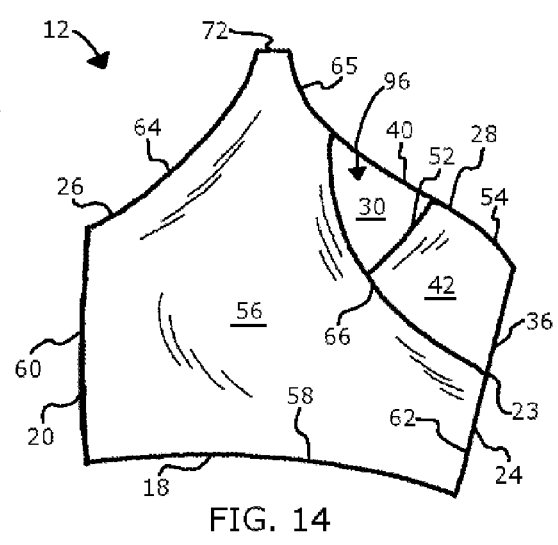
FIG. 14 is a back elevational view of the bottom layer, the middle layer, and the top layer of the left-side multifunction brassiere cup according to the first embodiment and is a mirror view of the back elevational view of the bottom layer, the middle layer, and the top layer of the right-side multifunction brassiere cup according to the first embodiment.

FIG. 16 shows the cup 12 incorporated in the brassiere 10 and further including edging 82 around the cup upper central edge 26 (FIG. 14) and cup upper outer edge 28 (FIG. 14). The edging 82 is continued along the adjustable back band 78. Edging 82 (see FIG. 25) is further included along the top layer lower edge 32 (FIG. 11). Further, a frame support 80 is included along the cup lower edge 18 (FIG. 14). According to the illustrated embodiment, the frame support 80 includes an elastic band configured to provide additional support for the wearer of the brassiere 10. In other embodiments, the frame support 80 may include an underwire, ribbing, or the like.

Figure 17:
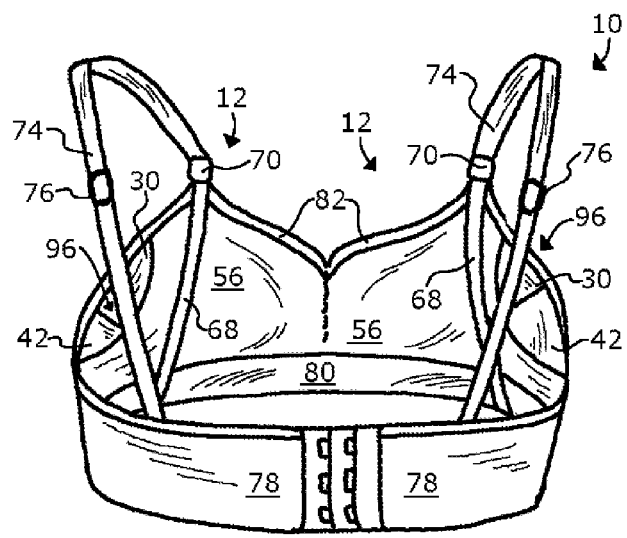
FIG. 17 is a perspective, back view of the brassiere with multifunction brassiere cups according to the first embodiment.
Figure 18:
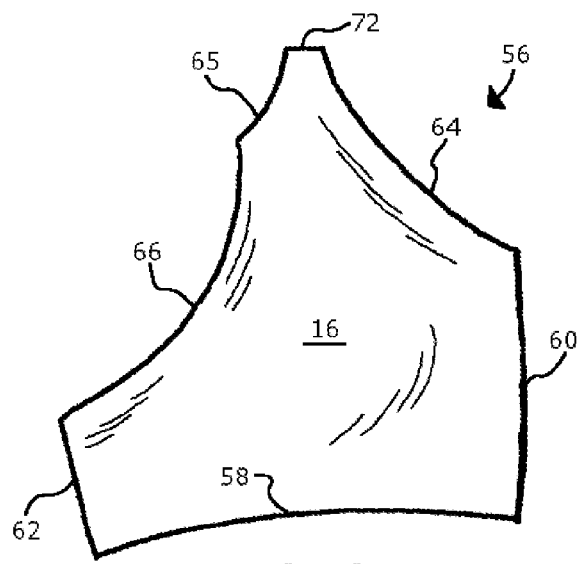
FIG. 18 is a front elevational view of the bottom layer of the left-side multifunction brassiere cup according to the first embodiment and is a mirror view of the front elevational view of the bottom layer of the right-side multifunction brassiere cup according to the first embodiment.
Figure 19:
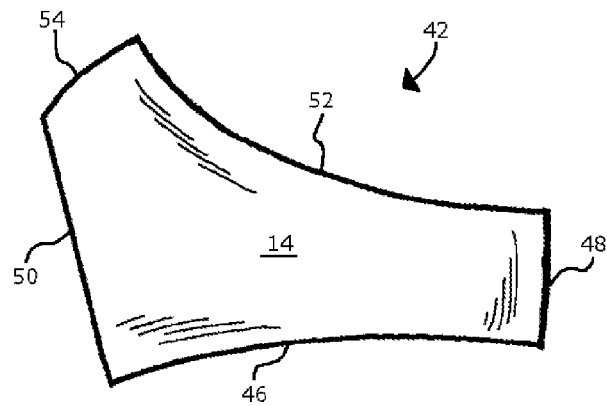
FIG. 19 is a front elevational view of the middle layer of the left-side multifunction brassiere cup according to the first embodiment and is a mirror view of the front elevational view of the middle layer of the right-side multifunction brassiere cup according to the first embodiment.
Figure 20:
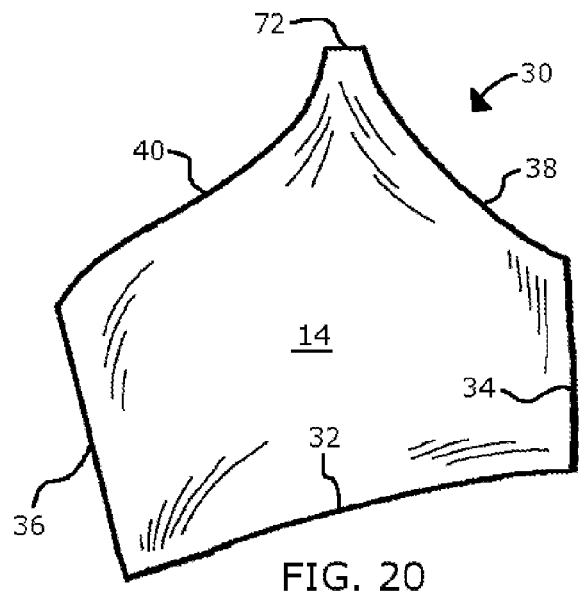
FIG. 20 is a front elevational view of the top layer of the left-side multifunction brassiere cup according to the first embodiment and is a mirror view of the front elevational view of the top layer of the right-side multifunction brassiere cup according to the first embodiment.
Figure 21:
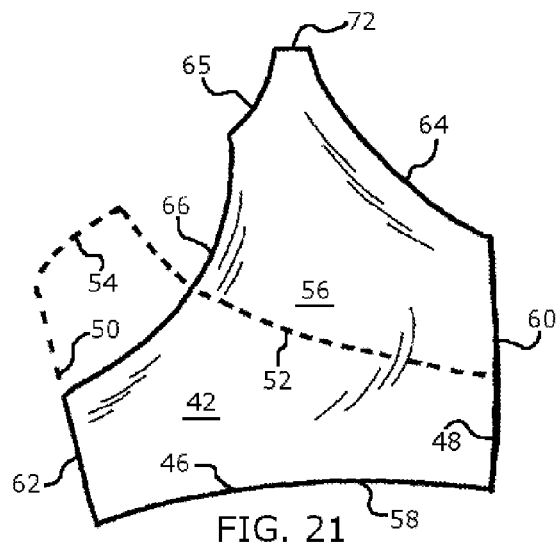
FIG. 21 is a front elevational view of the middle layer, shown in dashed line, overlapping the bottom layer of the left-side multifunction brassiere cup according to the first embodiment and is a mirror view of the front elevational view of the middle layer, shown in dashed line, overlapping the bottom layer of the right-side multifunction brassiere cup according to the first embodiment.
Figure 22:
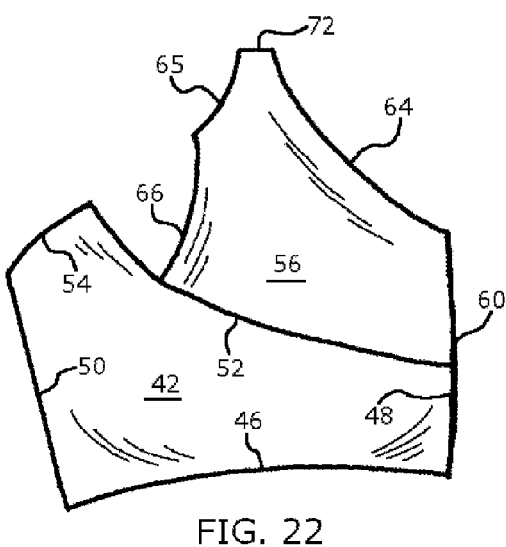
FIG. 22 is a front elevational view of the middle layer overlapping the bottom layer of the left-side multifunction brassiere cup according to the first embodiment and is a mirror view of the front elevational view of the middle layer overlapping the bottom layer of the right-side multifunction brassiere cup according to the first embodiment.
Figure 23:
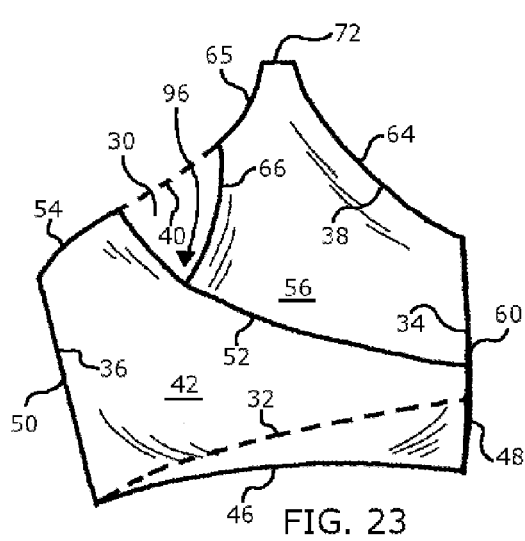
FIG. 23 is a front elevational view of the top layer, shown in dashed line, overlapping the middle layer and the bottom layer of the left-side multifunction brassiere cup according to the first embodiment and is a mirror view of the front elevational view of the top layer, shown in dashed line, overlapping the middle layer and the bottom layer of the right-side multifunction brassiere cup according to the first embodiment.
Figure 24:
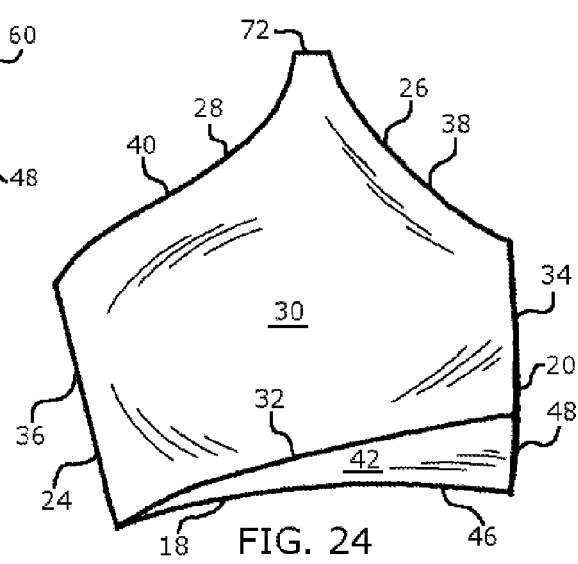
FIG. 24 is a front elevational view of the top layer overlapping the middle layer and the bottom layer of the left-side multifunction brassiere cup according to the first embodiment and is a mirror view of the front elevational view of the top layer overlapping the middle layer and the bottom layer of the right-side multifunction brassiere cup according to the first embodiment.
Figure 25:
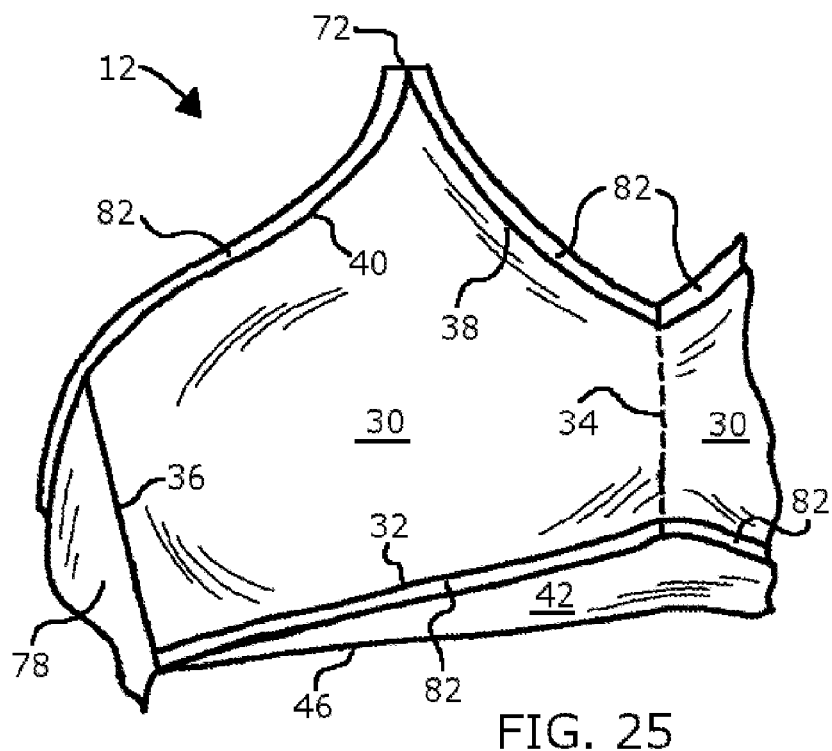
FIG. 25 is a partial, front elevational view of the left-side multifunction brassiere cup incorporated within the brassiere according to the first embodiment and is a mirror view of a partial, front elevational view of the right-side multifunction brassiere cup incorporated within the brassiere according to the first embodiment.
Figure 26:
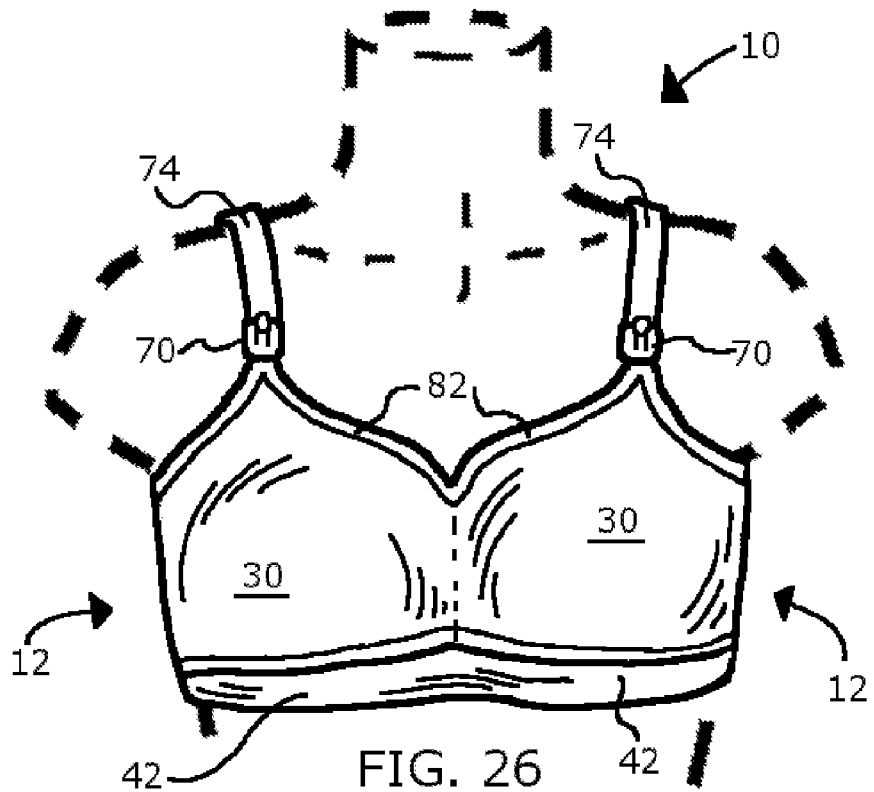
FIG. 26 is a front elevational view of a pair of multifunction brassiere cups incorporated within the brassiere according to the first embodiment.
Figure 27:
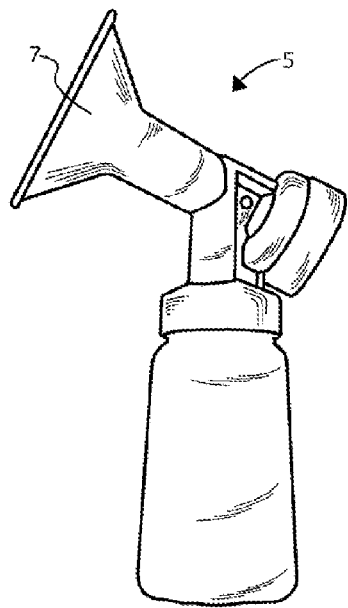
FIG. 27 is a side elevation view of a funnel and a reservoir of a conventional breast pump.
Figure 33:
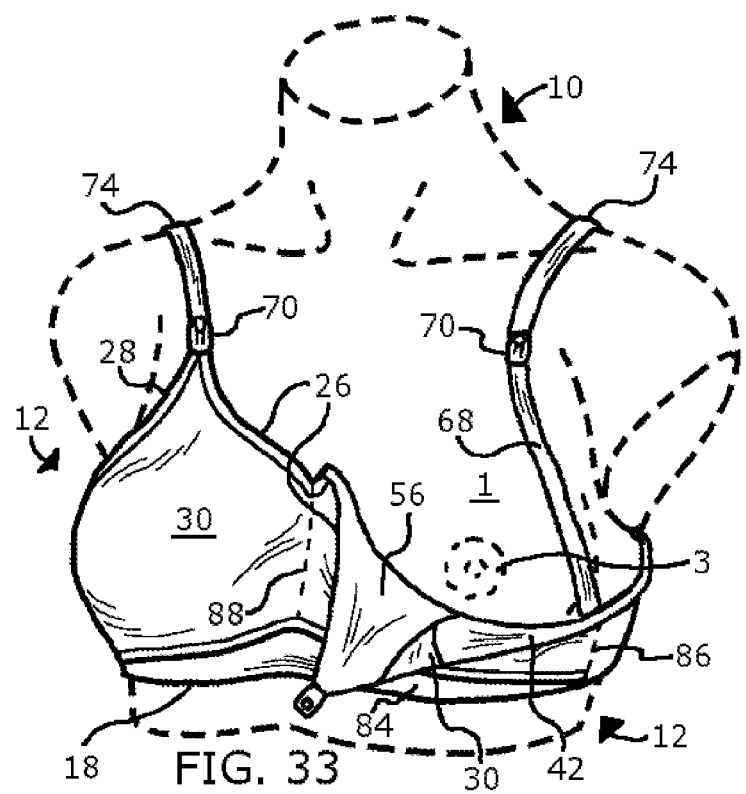
FIG. 33 is a perspective, front elevational view of the brassiere with multifunction brassiere cups according to the first embodiment with one selectively releasable clasp unclasped.
Figure 34:
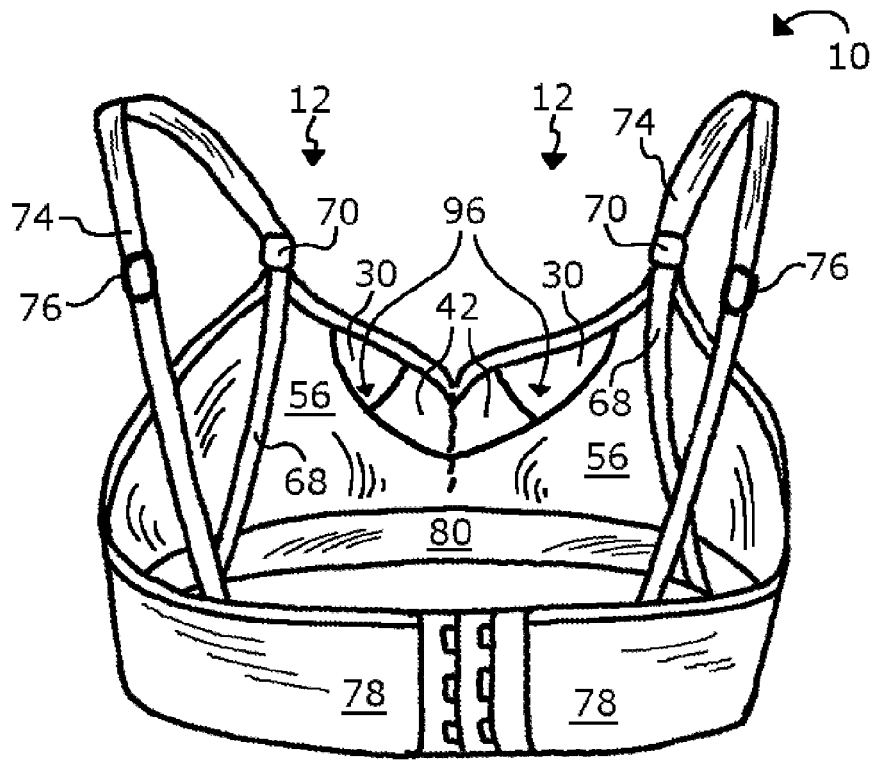
FIG. 34 is a perspective, back view of a brassiere with multifunction brassiere cups according to a third embodiment.

The cup 12 may be incorporated in a brassiere (e.g., brassiere 10) configured to accommodate nursing of an infant directly from the breast 1 (see FIG. 33). As shown in FIGS. 16 and 17, according to the first embodiment, the brassiere 10 includes a pair of selectively releasable clasps 70 (see also FIGS. 1 through 4), each attached to one of the cups 12 at one of the clasp attachment points 72 and also connected to one of the shoulder straps 74. Each selectively releasable clasp 70 is configured to selectively connect one of the shoulder straps 74 to one of the cups 12. Each selectively releasable clasp 70 is configured to be selectively unclasped so as to disconnect its respective shoulder strap 74 from its respective cup 12 so as to allow the layers of the cup 12 to be let down away from the shoulder strap 74, thereby uncovering the breast 1 (FIG. 33) and nipple 3 (FIG. 33) so as to allow for direct nursing of an infant from the breast 1, as shown in FIG. 33. The brassiere 10 may further include a pair of side support straps 68, with one side support strap 68 connecting one of the shoulder straps 74 to the cup lower edge 18 (FIG. 14) area of the brassiere 10. As shown in FIGS. 16 and 17, the side support straps 68 connect the shoulder strap 74 to the frame support 80. Accordingly, when one of the selectively releasable clasps 70 is selectively unclasped, the side support strap 68 provides continued connection between the respective shoulder strap 74 and the cup lower edge 18 area of the brassiere 10 such that the shoulder strap 74 remains secured in its place on the shoulder. In some embodiments, the side support strap 68 may be further configured to provide continued support for the breast 1 when the selectively releasable clasp 70 is selectively unclasped. The selectively releasable clasp 70 can then be reclasped to return the brassiere 10 to its original form. Therefore, the brassiere 10 may be configured to accommodate direct nursing of an infant with manipulation of only one clasp, without having to separate the layers of the cup 12 from one another, without having to remove the brassiere 10, without having to detach the cup 12 from the brassiere 10, and without having to detach any other part of the brassiere 10 from the brassiere 10.

While the back views of the layers of the brassiere 10 are illustrated in FIGS. 7 through 17, FIGS. 18 through 26 depict the front views of the layers. Again, these figures depict the front views of the left-side cup 12, such as the cup 12 shown to the left-hand side of FIG. 1. Comparing FIG. 8 with FIG. 19, it should be noted that, according to the first illustrated embodiment, the exterior side of the middle layer 42 may be made of the first material 14 while the interior side of the middle layer 42 may be made of the second material 16. Further, the exterior sides of the middle layer 42 and the top layer 30 may be made from the same first material 14 thereby allowing the cup 12 to be visually unified when viewed from the front while worn.

Figure 28:
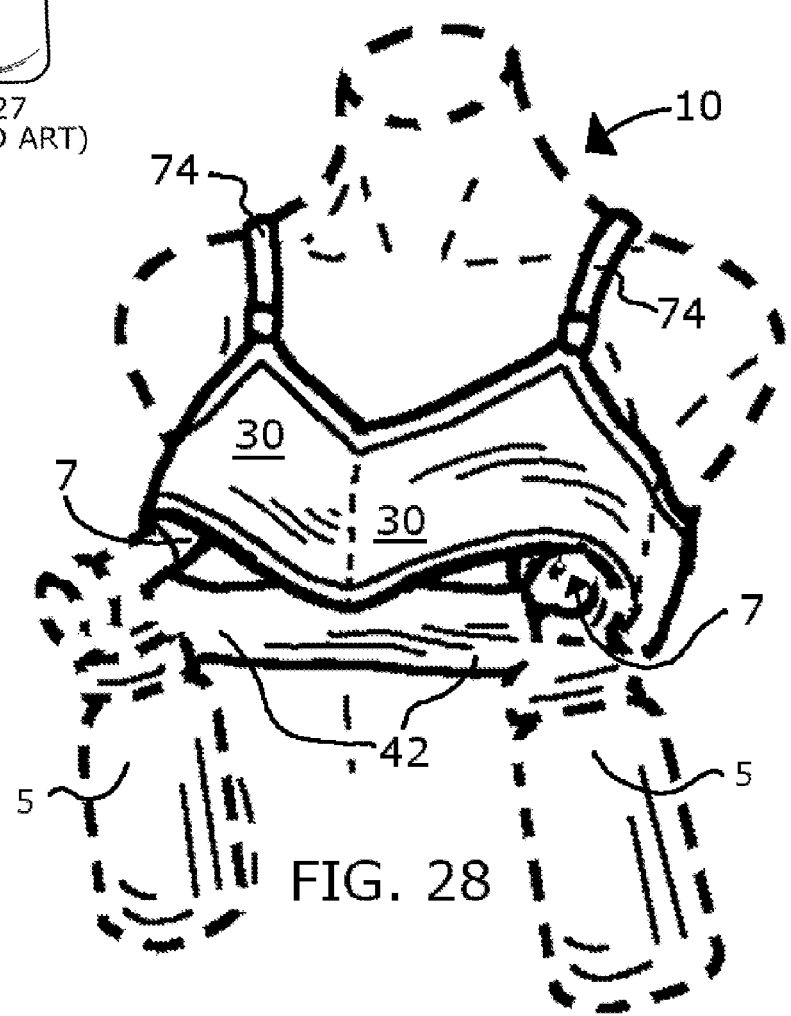
FIG. 28 is a perspective, front elevational view of the brassiere with multifunction brassiere cups according to the first embodiment with a funnel of a breast pump received by each cup.
Figure 29:
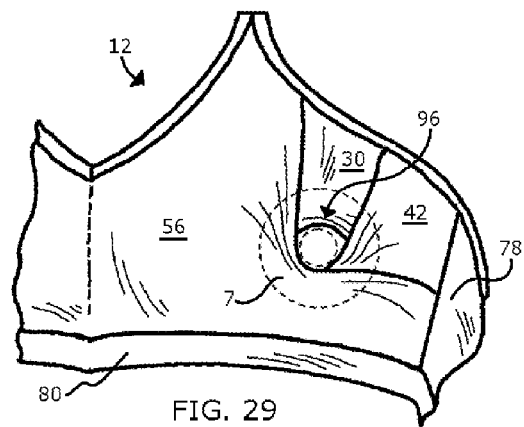
FIG. 29 is a partial, back elevational view of the left-side multifunction brassiere cup incorporated within the brassiere according to the first embodiment and a mirror view of a partial, back elevational view of the right-side multifunction brassiere cup incorporated within the brassiere according to the first embodiment, with a funnel of a breast pump received in the cup and located in a first position.
Figure 30:
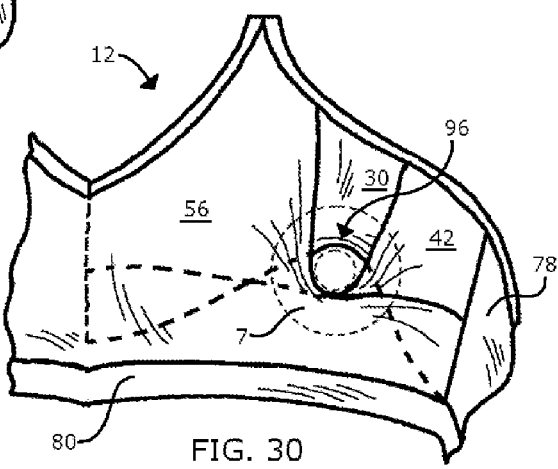
FIG. 30 is a partial, back elevational view of the left-side multifunction brassiere cup incorporated within the brassiere according to the first embodiment and a mirror view of a partial, back elevational view of the right-side multifunction brassiere cup incorporated within the brassiere according to the first embodiment, with a funnel of a breast pump received in the cup and located in the first position with some edges of the middle and top layers shown in dashed line.
Figure 31:
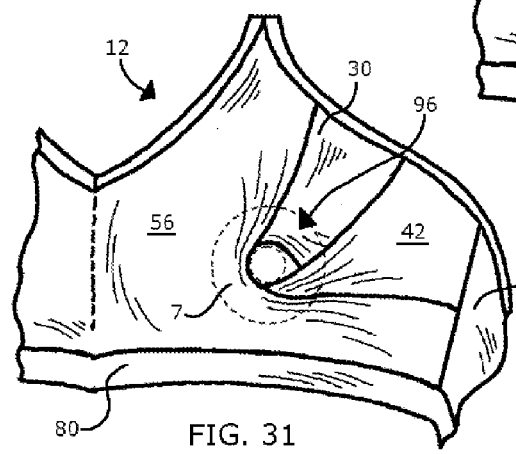
FIG. 31 is a partial, back elevational view of the left-side multifunction brassiere cup incorporated within the brassiere according to the first embodiment and a mirror view of a partial, back elevational view of the right-side multifunction brassiere cup incorporated within the brassiere according to the first embodiment, with a funnel of a breast pump received in the cup and located in a second position.
Figure 32:
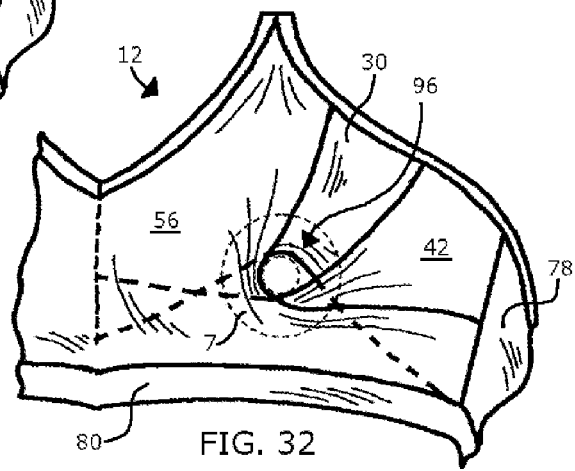
FIG. 32 is a partial, back elevational view of the left-side multifunction brassiere cup incorporated within the brassiere according to the first embodiment and a mirror view of a partial, back elevational view of the right-side multifunction brassiere cup incorporated within the brassiere according to the first embodiment, with a funnel of a breast pump received in the cup and located in the second position with some edges of the middle and top layers shown in dashed line.

As shown in FIG. 28, the cup 12 is configured to support a funnel (e.g., funnel 7) of a conventional breast pump and reservoir (e.g., the breast pump and reservoir 5 shown in FIG. 27) against the nipple 3 of a breast (e.g., breast 1). More particularly, the cup 12 is configured to selectively receive the funnel 7 behind the unattached edge of the top layer 30 and within the nook 96 defined by the unattached edges of the middle layer 42 and the bottom layer 56. According to the first illustrated embodiment, therefore, the funnel 7 may be received behind the top layer lower edge 32 and within the nook 96 defined by the middle layer upper central edge 52 and the bottom layer upper outer edge 66.

The top layer 30, the middle layer 42, and the bottom layer 56 may all be made of a uniformly stretchable material, such as spandex, LYCRA®, nylon, or the like, or blends thereof. In other embodiments, the top layer 30 and the bottom layer 56 are made of a uniformly stretchable material while the middle layer 42 is not made of a stretchable material. In other embodiments, only the unattached edges of the top layer 30, the middle layer 42, and the bottom layer 56 are made of a stretchable material, such as a band of elastic. In still other embodiments, only the unattached edges of the top layer 30 and the bottom layer 56 are made of a stretchable material. In any regard, the unattached edges of at least two layers are configured to be stretched away from their respective non-stretched shapes to accommodate insertion of the funnel 7 within the nook 96 and underneath the unattached edge of the top layer 30. According to the first illustrated embodiment, to receive the funnel 7 within the cup 12, the top layer lower edge 32 is stretched away from the cup lower edge 18, allowing the funnel 7 to be inserted underneath and behind the top layer 30. The middle layer upper central edge 52 is stretched away from the cup side central edge 20 to allow the funnel 7 to be inserted behind the middle layer 42. The bottom layer upper outer edge 66 is stretched away from the cup upper outer edge 28 to allow the funnel 7 to be inserted behind the bottom layer 56 and within the nook 96.

As shown in FIGS. 29 through 32, when the funnel 7 is received within the cup 12, the funnel 7 is supported against the nipple 3 of the breast 1 by each of the unattached edges of the top layer 30, the middle layer 42, and the bottom layer 56. Thus, according to the first illustrated embodiment, the funnel 7 is supported by each of the top layer lower edge 32, the middle layer upper central edge 52, and the bottom layer upper outer edge 66. The majority of the surface of the funnel 7 may be contacted and supported by the top layer 30, the middle layer 42, and the bottom layer 56, accommodating sufficient stability of the funnel 7 against the nipple 3. Because the top layer 30, the middle layer 42, and the bottom layer 56 may all be made of a uniformly stretchable material, stretching the layers to insert the funnel 7 may lead to each unattached edge of the layers elastically resisting additional stretch of the edge. Accordingly, the unattached edge of the top layer 30 urges the funnel 7 toward the direction of the non-stretched unattached edge of the top layer 30, e.g., toward the cup lower edge 18; the unattached edge of the middle layer 42 urges the funnel 7 toward the direction of the non-stretched unattached edge of the middle layer 42, e.g., toward the cup upper central edge 26; while the unattached edge of the bottom layer 56 urges the funnel 7 toward the direction of the non-stretched unattached edge of the bottom layer 56, e.g., toward the cup upper outer edge 28. Thus, the three-direction pulls hold the funnel 7 in tension where the funnel 7 is positioned over the nipple 3, even as milk is expressed from the breast 1 and the reservoir of the breast pump 5 is filled and becomes heavier. Further, as each of the layers is somewhat stretched away from the chest to accommodate the breast 1 and the funnel 7, each layer urges the funnel 7 to remain pressed against the nipple 3 and breast 1. Accordingly, the funnel 7 is supported not only in three directions along the surface of the cup 12, but also in a direction perpendicular to the surface of the cup 12. The cup 12 is further configured to allow the funnel 7 to be supported at the location of the nipple 3, regardless of whether the nipple 3 is located in the center of the breast 1, such that the funnel 7 may be supported in the position shown in FIGS. 31 and 32, or somewhat off to the side of the center of the breast 1, such that the funnel 7 may be supported in the position shown in FIGS. 29 and 30. Accordingly, the cup 12 may be comfortably utilized throughout the full range of naturally-occurring nipple 3 placements. Also, the elasticity of the material of the layers or the unattached edging accommodates the natural expansion and contraction of a nursing woman's breasts.

While, according to the first and second illustrated embodiments, the unattached edge of the top layer 30 is shown as being proximate to the cup lower edge 18, the unattached edge of the middle layer 42 is shown as extending upwardly from the cup side central edge 20 to the cup upper outer edge 28, and the unattached edge of the bottom layer 56 is shown as extending upwardly from the cup side outer edge 24 to the cup upper outer edge 28, thereby defining the nook 96 along the cup upper outer edge 28, in other embodiments, the unattached edges may be differently arranged. As an example, according to a third illustrated embodiment, shown in FIG. 34, the unattached edge of the top layer 30 may be proximate to the cup lower edge 18 (FIG. 14), the unattached edge of the middle layer 42 may extend upwardly from the cup side outer edge 24 (FIG. 14) to the cup upper central edge 26 (FIG. 14), and the unattached edge of the bottom layer 56 may extend upwardly from the cup side central edge 20 (FIG. 14) to the cup upper central edge 26 (FIG. 14). In any regard, the unattached edge of the middle layer 42 crosses the unattached edge of the bottom layer 56 to define the nook 96, and the top layer 30 covers the nook 96.

In some embodiments, when the cup 12 is incorporated in a brassiere (e.g., brassiere 10), a pair of cups 12 are included, for example, the above-described left-side cup 12 and a right-side cup 12. (It should be noted that while FIGS. 7 through 16 and 18 through 25 show the left-side cup 12, the views of the right-side cup 12 would simply be mirror-images of these figures.) Further, according to the illustrated embodiments, the top layers 30 of the left-side and right-side cups 12 may be made from a single piece of material. Likewise, the middle layers 42 of the left-side and right-side cups 12 may be made from a single piece of material, and the bottom layers 56 of the left-side and right-side cups 12 may be made from a single piece of material.

Figure 4:
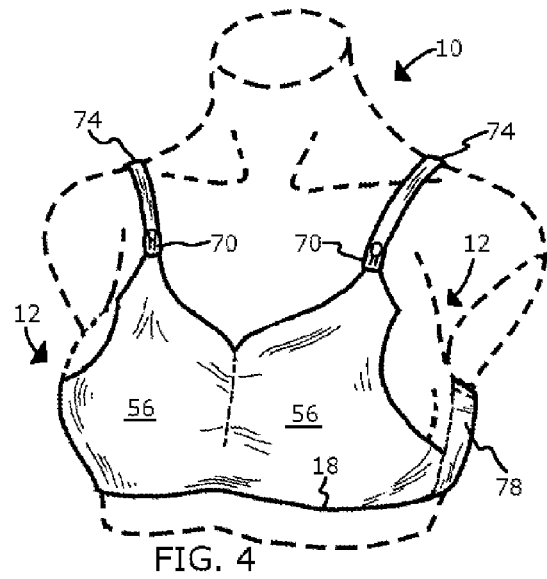
FIG. 4 is a perspective, front elevational view of the brassiere with multifunction brassiere cups according to the first embodiment with the top layer and a middle layer removed.

Also, according to the illustrated embodiments, the bottom layer 56 may be configured to cover the nipple 3 of the breast 1 and a majority of the breast 1 when the bottom layer 56 is not stretched, as shown in FIG. 4. As such, when and if the top layer 30 is stretched back from its non-stretched position and from the cup lower edge 18, the nipple 3 will not be exposed. Further, as the bottom layer 56 may be the first layer adjacent to the nipple 3 and the breast 1, because the bottom layer 56 covers the nipple 3 in its non-stretched form, the edges of the bottom layer 56 may not rub against or irritate the nipple 3. Preferably, no seams are included inside the edges of the layers, which may avoid irritating the nipple 3.

Also according to the illustrated embodiments, the top layer 30 may be configured to cover the nipple 3 of the breast 1 and the majority of the breast 1 when the top layer 30 is not stretched, as shown in FIG. 1. As such, the appearance of the cup 12 and brassiere 10 before the funnel 7 is received by the cup 12 may be that of a conventional brassiere. In some embodiments, the middle layer 42 may be further configured to cover the nipple 3 of the breast 1 when the middle layer 42 is not stretched.

The exemplary embodiments illustrated in the figures and described above illustrate, but do not limit, the present disclosure. It should be understood that there is no intention to limit the multifunction brassiere cup to the specific forms disclosed; rather, the multifunction brassiere cup is to cover all modifications, alternative constructions, and equivalents falling within the spirit and scope of the present disclosure. For example, while the exemplary embodiments illustrate the incorporation of the multifunction brassiere cup within a brassiere including two such multifunction brassiere cups, the multifunction brassiere cup is not limited to use in pairs, but may be used in a brassiere having, as the other cup, a conventional cup not configured to receive the funnel of a breast pump. Further, in other embodiments, a nursing pad may be inserted between the top layer and another of the layers or between the breast and the bottom layer. Still further, while in the illustrated embodiments, the first layer is illustrated as a top layer that directly partially overlaps the second layer (e.g., a middle layer) that directly partially overlaps the third layer (e.g., a bottom layer), in other embodiments the ordering of the layers may be reversed, as, for example, the first layer partially overlapping the third layer that partially overlaps the second layer that rests against the breast. Hence, the foregoing description should not be construed to limit the scope of the present disclosure, including the following claims. Accordingly, while there is shown and described the present illustrated embodiments of the multifunction brassiere cup, it is to be distinctly understood that the present disclosure is not limited thereto but may be variously embodied to be practiced within the scope of the following claims. From the foregoing description, it will be apparent that various changes may be made without departing from the spirit and scope of the following claims.

The invention claimed is:

1. A brassiere comprising a cup configured to support a funnel of a breast pump against a nipple of a breast, the cup comprising:
   a first layer comprising a first layer unattached edge extending to a periphery of the cup;
   a second layer partially overlapping the first layer and connecting to the first layer, the second layer comprising a second layer unattached edge extending to the periphery of the cup, the second layer unattached edge crossing over the first layer unattached edge to define a nook; and
   a third layer partially overlapping the second layer and the first layer and covering the nook, the third layer connecting to the second layer and the first layer, the third layer comprising a third layer unattached edge;
   the cup configured to selectively receive the funnel behind the third layer unattached edge and within the nook behind the second layer unattached edge and the first layer unattached edge; and
   each of the third layer unattached edge, the second layer unattached edge, and the first layer unattached edge configured to engage at least one area of a funnel when received in the cup to support the funnel against the nipple.

2. The brassiere of claim 1, wherein the first layer and the third layer each comprise a stretchable material.

3. The brassiere of claim 2, wherein the first layer is configured to cover the nipple of the breast and a majority of the breast when the first layer is not stretched for engaging the at least one area of the funnel.

4. The brassiere of claim 2, wherein the third layer is configured to cover the nipple of the breast and a majority of the breast when the third layer is not stretched for engaging the at least one area of the funnel.

5. The brassiere of claim 1, wherein the first layer unattached edge and the third layer unattached edge are stretchable.

6. The brassiere of claim 5, wherein the first layer is configured to cover the nipple of the breast and a majority of breast when the first layer unattached edge is not stretched for engaging the at least one area of the funnel.

7. The brassiere of claim 5, wherein the third layer is configured to cover the nipple of the breast and a majority of the breast when the third layer unattached edge is not stretched for engaging the at least one area of the funnel.

8. The brassiere of claim 1, further comprising a frame support connected to the first layer and the second layer along a cup lower edge.

9. A brassiere for supporting a funnel of a breast pump against a nipple of a breast, the brassiere comprising:
   a pair of cups, each cup of the pair of cups comprising:
      a bottom layer comprising a bottom layer unattached edge;
      a middle layer partially overlapping the bottom layer and connecting to the bottom layer, the middle layer comprising a middle layer unattached edge crossing over the bottom layer unattached edge to define a V-shaped nook; and
      a top layer partially overlapping the middle layer and the bottom layer and covering the V-shaped nook, the top layer connecting to the middle layer and the bottom layer, the top layer comprising a top layer unattached edge;
   each cup of the pair of cups configured to selectively receive the funnel behind the top layer unattached edge and within the V-shaped nook behind the middle layer unattached edge and the bottom layer unattached edge; and
   the top layer unattached edge, the middle layer unattached edge, and the bottom layer unattached edge contacting the funnel at different areas of the funnel when the funnel is received in a cup of the pair of cups.

10. The brassiere of claim 9, wherein the bottom layer and the top layer comprise a stretchable material.

11. The brassiere of claim 10, wherein the bottom layer covers the nipple of the breast and a majority of the breast when the bottom layer is not stretched for receiving the funnel.

12. The brassiere of claim 10, wherein the top layer covers the nipple of the breast and a majority of the breast when the top layer is not stretched for receiving the funnel.

13. The brassiere of claim 9, wherein the bottom layer unattached edge and the top layer unattached edge are stretchable.

14. The brassiere of claim 13, wherein the bottom layer covers the nipple of the breast and a majority of the breast when the bottom layer unattached edge is not stretched for receiving the funnel.

15. The brassiere of claim 13, wherein the top layer covers the nipple of the breast and a majority of the breast when the top layer unattached edge is not stretched for receiving the funnel.

16. The brassiere of claim 9, further comprising a pair of shoulder straps each connected to one cup of the pair of cups.

17. The brassiere of claim 16, further comprising a pair of selectively releasable clasps each configured to selectively connect one shoulder strap of the pair of shoulder straps to one cup of the pair of cups, wherein selective release of one selectively releasable clasp of the pair of selectively releasable clasps accommodates uncovering of the breast to accommodate nursing of an infant directly from the breast.

18. The brassiere of claim 17, further comprising a pair of side support straps each connecting one selectively releasable clasp of the pair of selectively releasable clasps to a cup lower edge, wherein, following selective release of the one selectively releasable clasp, the one shoulder strap of the pair of shoulder straps remain in place.

19. A brassiere for supporting a funnel of a breast pump against a nipple of a breast expressing milk, the brassiere comprising:
   a pair of cups, each cup of the pair of cups having a cup lower edge, a cup side central edge, a cup side outer edge, a cup upper central edge, and a cup upper outer edge; each cup of the pair of cups comprising:
      a bottom layer comprising:
         a bottom layer lower edge aligning along the cup lower edge;
         a bottom layer side central edge extending from the bottom layer lower edge and aligning along the cup side central edge;
         a bottom layer upper central edge extending from the bottom layer side central edge and aligning along the cup upper central edge;
         a bottom layer side outer edge extending from the bottom layer lower edge and aligning along part of the cup side outer edge;
         a bottom layer upper outer edge extending from the bottom layer side outer edge; and
         a bottom layer upper clasp edge extending from the bottom layer upper outer edge and aligning along part of the cup upper outer edge;

a middle layer partially overlapping the bottom layer and comprising:
  a middle layer lower edge aligning along the cup lower edge;
  a middle layer side central edge extending from the middle layer lower edge and aligning along part of the cup side central edge;
  a middle layer upper central edge extending from the middle layer side central edge;
  a middle layer upper outer edge extending from the middle layer upper central edge and aligning along part of the cup upper outer edge; and
  a middle layer side outer edge extending from the middle layer upper outer edge to the middle layer lower edge and aligning along the cup side outer edge;
  the middle layer upper central edge arranged so as to cross over the bottom layer upper outer edge to define a nook; and
a top layer partially overlapping the middle layer and the bottom layer and covering the nook, the top layer comprising:
  a top layer lower edge;
  a top layer side central edge extending from the top layer lower edge and aligning along part of the cup side central edge;
  a top layer upper central edge extending from the top layer side central edge and aligning along the cup upper central edge;
  a top layer side outer edge extending from the top layer lower edge and aligning along the cup side outer edge; and
  a top layer upper outer edge extending from the top layer side outer edge and aligning along the cup upper outer edge;
the bottom layer and the middle layer connecting at the cup lower edge along the bottom layer lower edge and the middle layer lower edge;
the bottom layer, the middle layer, and the top layer connecting at the cup side central edge along the bottom layer side central edge, the middle layer side central edge, and the top layer side central edge;
the bottom layer and the top layer connecting at the cup upper central edge along the bottom layer upper central edge and the top layer upper central edge;
the bottom layer and the top layer connecting at part of the cup upper outer edge along the bottom layer upper clasp edge and part of the top layer upper outer edge;
the middle layer and the top layer connecting at part of the cup upper outer edge along the middle layer upper outer edge and part of the top layer upper outer edge;
the bottom layer, the middle layer, and the top layer connecting at the cup side outer edge along the bottom layer side outer edge, the middle layer side outer edge, and the top layer side outer edge;
the bottom layer upper outer edge being unattached to the middle layer and the top layer;
the middle layer upper central edge being unattached to the bottom layer and the top layer;
the top layer lower edge being unattached to the middle layer and the bottom layer; and
each cup of the pair of cups configured to selectively receive the funnel behind the top layer lower edge and within the nook behind the middle layer upper central edge and the bottom layer upper outer edge such that the funnel is supported against the nipple each of the top layer lower edge, the middle layer upper central edge, and the bottom layer upper outer edge.

20. The brassiere of claim 19, wherein:
the bottom layer upper outer edge and the top layer lower edge are stretchable;
the bottom layer is configured to cover the nipple of the breast and a majority of the breast when the bottom layer upper outer edge is not stretched for receiving the funnel within the nook; and
the top layer is configured to cover the nipple of the breast and the majority of the breast when the top layer lower edge is not stretched for receiving the funnel behind the top layer lower edge.

\* \* \* \* \*

UNITED STATES PATENT AND TRADEMARK OFFICE
CERTIFICATE OF CORRECTION

| | | |
|---|---|---|
| PATENT NO. | : 8,469,770 B2 | Page 1 of 1 |
| APPLICATION NO. | : 12/785426 | |
| DATED | : June 25, 2013 | |
| INVENTOR(S) | : Dawn Michele Alva | |

It is certified that error appears in the above-identified patent and that said Letters Patent is hereby corrected as shown below:

In the specification:
    COLUMN 7,    LINE 9,    change "FIG 2." to --FIG. 2.--

In the claims:
CLAIM 6,    COLUMN 13,  LINE 42,    change "breast when" to --the breast when--
CLAIM 19,  COLUMN 16,  LINE 26,    change "nipple each" to --nipple by each--

Signed and Sealed this
Third Day of June, 2014

Michelle K. Lee
*Deputy Director of the United States Patent and Trademark Office*